United States Patent [19]

Knepper

[11] Patent Number: 4,617,299

[45] Date of Patent: Oct. 14, 1986

[54] METHOD FOR THE PREVENTION OF OCULAR HYPERTENSION, TREATMENT OF GLAUCOMA AND TREATMENT OF OCULAR HYPERTENSION

[76] Inventor: Paul A. Knepper, 175 E. Delaware St., Chicago, Ill. 60611

[21] Appl. No.: 663,507

[22] Filed: Oct. 22, 1984

Related U.S. Application Data

[63] Continuation-in-part of Ser. No. 562,843, Dec. 19, 1983, abandoned.

[51] Int. Cl.[4] .................... A61K 31/56; A61K 31/35
[52] U.S. Cl. .................................... 514/178; 514/453
[58] Field of Search .................. 424/238, 243, 279; 514/178, 453

[56] References Cited

PUBLICATIONS

Lamble et al; Exp. Eye Res., vol. 26 (1978) pp. 599–610.
"Steroids" by Fieser et al., p. 519.
Modern Drug. Encyclopedia (1975) pp. 577, 578, 579 and 780.

*Primary Examiner*—Elbert L. Roberts
*Attorney, Agent, or Firm*—Dressler, Goldsmith, Shore, Sutker & Milnamow, Ltd.

[57] ABSTRACT

A novel pharmacologic therapy for treatment of idiopathic primary open angle glaucoma, drug-induced glaucoma and elevated intraocular pressure is disclosed. The pharmacologic therapy consists of a novel composition comprised of a selected anabolic androgenic compound and a physiologically tolerable carrier. In accordance with a method aspect of this invention, the pharmacologic substance is administered to the eye of a warm blooded animal in such a manner as to maintain physiologic or normal intraocular pressure, or to return elevated intraocular pressure to normal levels. The method aspect of this invention may also be employed to prevent drug induced elevated intraocular pressure.

28 Claims, No Drawings

METHOD FOR THE PREVENTION OF OCULAR HYPERTENSION, TREATMENT OF GLAUCOMA AND TREATMENT OF OCULAR HYPERTENSION

CROSS REFERENCE TO RELATED APPLICATION

This is a Continuation-In-Part of co-pending Application Ser. No. 562,843 filed Dec. 19, 1983, now abandoned.

TECHNICAL FIELD OF THE INVENTION

The present invention relates to regulation of intraocular pressure, and more particularly to a novel composition and method for prevention or reduction of elevated intraocular pressure such as found in glaucoma by the use of corticosteroid anti-inflammatory agents.

BACKGROUND OF THE INVENTION

Glaucoma is one of the leading causes of irreversible blindness. Although the occurrence of glaucoma is more frequent in the elderly, the disease affects all age groups. Glaucoma is a significant cause of visual impairment and results in significant loss of productivity in affected individuals. Glaucoma is not a single disease process, although it may simply be characterized as a condition where the intraocular pressure (IOP) is too high for the normal functioning of the optic nerve. Damage to the optic nerve is associated with progressive loss of visual field, and if untreated can lead to total irreversible blindness.

As the term glaucoma encompasses several disease states, the causes of glaucoma are many. This invention is directed toward the treatment of one class of glaucoma, primary open angle glaucoma, where there is a normal anterior chamber and an open anterior chamber angle. This disease state may occur spontaneously or may be secondary to treatment for another systemic disease state. An example of the latter is elevated intraocular pressure secondary to corticosteroid treatment for inflammation.

The administration of corticosteroid ocular anti-inflammatory agents has been linked to elevated intraocular pressure in the human eye [Armaly, Arch. Ophth., 70:482 (1963); Becker et al., Arch. Ophthal., 70:500 (1963); Nicholas, Arch. Ophthal., 72:189 (1964); Armaly, Arch. Ophthal., 70:492 (1963)]. Corticosteroid therapy for systemic inflammation may also induce elevated intraocular pressure. These compounds also are commonly administered to relieve ocular inflammation. These effects can be observed when one member of the class of corticosteroids is topically administered to normal and glaucomatous eyes. [Cantrill, et al., Am. J. Ophthal., 79:6:1012 (1975)]. The pressure elevating effect of topically applied corticosteroids has been successfully reproduced in rabbits [Levene,.et al., Am. J. Ophthal., 78:3:509 (1974); Bonomi, et al., Graefes Arch. Ophth., 209:73 (1978); Podos, Symp. on Eye Dis., 81:632 (1976); Knepper, et al., Exp. Eye Res., 27:567 (1978)].

Topical instillation of dexamethasone, (9-alpha-fluoro-16-methyl prednisolone) to the eye results in a condition similar to glaucoma; that is, elevation of intraocular pressure (IOP) in man. This undesirable side effect of corticosteroid treatment, if unchecked, may result in permanent debilitating effects upon the eye. These undesirable effects include visual field loss or other impairment of visual acuity resulting from optic nerve damage. These effects are similar to those seen in idiopathic primary open angle glaucoma. The similarity of corticosteroid induced glaucoma to idiopathic is primary open angle glaucoma coupled with the reproducible effects of corticosteroid dexamethasone induced glaucoma in the rabbit indicate that dexamethasone induced glaucoma is a good model of human primary open angle glaucoma as well as corticosteroid induced glaucoma.

A. Open Angle Glaucoma

Primary open angle glaucoma is the most common form of glaucoma. It is a major cause of blindness. Primary open angle glaucoma is characterized by elevated intraocular pressure which, if untreated, irreversibly damages the optic nerve. This results in impairment of visual field or loss of some or all of the affected individuals vision. Several researchers in the field have suggested that primary open angle glaucoma is caused by alteration in cortisol metabolism in the cells of the trabecular meshwork [Southren et al.; Invest. Ophthal., 24:1413 (1983)]. While the exact mechanism causing glaucoma is unknown, the physiologic effect of elevated intraocular pressure is found in spontaneous primary open angle glaucoma and corticosteroid induced open angle glaucoma. Spontaneously occurring primary open angle glaucoma is physiologically similar to the untoward intraocular pressure elevating side effect of corticosteroid administration.

The conventional therapeutic regime for primary open angle glaucoma or ocular hypertension typically includes topical administration of pilocarpine, epinephrine, anti-cholinergic agents and beta-adrenergic blocking agents administered alone or in combination. These drugs are believed to decrease the amount of aqueous humor formed by the eye, or decrease the resistance of aqueous humor drainage out of the eye, or both. The result is a decrease in intraocular pressure.

Unfortunately, the conventional therapies are often of limited success. Side effects of these therapies include blurred vision, irritation of the cornea and conjunctiva, and cataract formation. [Goodman and Gilman, The Pharmacological Basis of Therapeutics, 4th Ed., MacMillan Pub. (1970); Shields, A Study Guide for Glaucoma, Williams & Wilkins Pub. (1982)] Untoward systemic side effects also occur with the conventional therapies.

Carbonic anhydrase inhibitors in tablet form may be added to the treatment regime should the topical administration of the above-mentioned drugs be poorly tolerated or fail to reduce intraocular pressure [Shields, supra]. Unfortunately, carbonic anhydrase inhibitors present further opportunities for untoward side effects, such as drowsiness, paresthesias, renal calculi, bone marrow depression, and various allergic reactions.

Surgical intervention is recommended only where the maximum tolerable medical therapy fails to halt the progressive glaucomatous damage to the optic nerve resulting from elevated intraocular pressure. In these cases, surgery may be required due to medical failure of pharmacologic agents as a result of progressive glaucomatous damage to the optic nerve, drug intolerance, poor patient compliance with treatment regimes, or unsuccessful utilization of all forms of anti-glaucoma drugs. Surgery is attempted to create an alternative pathway for aqueous humor drainage or to laser-treat the trabecular meshwork (the aqueous humor filter). The long term success of surgical intervention is not uniform among patients so treated. Futhermore, the administration of anti-glaucoma agents is a life-long therapeutic regime with unknown ultimate ocular or systemic side effects that may result from the duration of treatment, combination of agents employed, drug interactions or acquired sensitivities to conventional anti-glaucoma preparations.

B. Risk Factors

Members of the population at risk for acquiring primary open angle glaucoma, the most common form of glaucoma, may present one or several risk factors. The incidence of primary open angle glaucoma increases with every advancing decade. There is a higher prevalance of the disease in males.

The onset of primary open angle glaucoma can be related to systemic disease states such as diabetes mellitus, Cushings syndrome, hypothyroidism, hemodynamic crises, hyper-coagulation disorders and alterations in systemic blood pressure. Close relatives of patients with primary open angle glaucoma are at a significantly higher risk than the general population according to several studies [Kolken et al., Israel J. Med. Dir. 81:357 (1972); Cameron et al., Glaucoma, LB Hunt ed. Edinburgh (1966); Shin et al., Arch. Ophthal., 95:598 (1977)]. Inheritance of a tendency to acquire glaucoma is believed to be by a polygenic, multifactorial mode. High myopes present an increased risk of disease [Schlossman, Intraocular Lens Med. J., 1:84 (1975)], although the relationship between myopia and glaucoma may be indicative of a longer period of onset or early glaucoma rather than truly higher intraocular pressure distribution throughout the myopic population.

Persons receiving corticosteroid therapy often acquire elevated introcular pressure subsequent to that therapy. Corticosteroid therapy places individuals at high risk for subsequent development of elevated intraocular pressure with subsequent glaucomatous symptomology. (Shields, supra.)

Other drug therapies may also cause increased intraocular pressure. Thus ACTH, glucocorticoids and growth hormone may cause a secondary elevation of intraocular pressure. Hypothyroidism has been associated with glaucoma.

A reproducible correlation between topical corticosteroid therapy and elevated intraocular pressure has been established. Elevated intraocular pressure is one of the major adverse side effects of corticosteroid treatment for systemic or ocular disease states. (Shields, supra; Goodman and Gilman, supra).

Many primary open angle glaucoma patients and ocular hypertensives suffer even greater elevation of intraocular pressure when topical corticosteriods are administered as anti-inflammatory agents. A positive correlation between the administration of corticosteriods such as dexamethasone resulting in elevated intraocular pressure has been established. [Armaly, Arch. Ophthal., 70:492 (1963); Godel et al., Ann. Ophthal., 3:191 (1978); Cantrill et al., Am J. Ophthal., 79:6:1012 (1975); Shields, supra].

C. Induced Elevated Intraocular Pressure

Corticosteriod glaucoma in humans (secondary glaucoma) closely resembles the spontaneous disease state of primary open angle glaucoma. Animal models of this disease state have been successfully obtained through the topical instillation of glucocorticoids and corticosteroids such as dexamethasone [Knepper et al., supra]. Rabbits are the primary experimental animals of choice because of similarities in physiology of aqueous humor dynamics, the ready availability of the animals, and suitability for accurate tonometry [Bonomi, Graefes Archiv. Ophthal., 209:73 (1978)]. Successful induction of increased intraocular pressure in the rabbit has been accomplished by a number of researchers utilizing corticosteroids. This has resulted in the conclusion that the rabbit is a good model of corticosteriod induced glaucoma, and that this induced disease state is a good model for investigation of treatment regimes as would be applied to human primary open angle glaucoma [Bonomi, supra; Levene, supra; Southren et al., Invest. Ophthal., 15:3:222 (1976); Knepper et al., Exp. Eye Res., 27:567 (1978); Podos supra]. A variety of routes of administration of corticosteroids produce elevated IOP such as is seen in primary open angle glaucoma, however, topical application to the eye is particularly effective in increasing intraocular pressure.

D. Aqueous Outflow Resistance

The primary site of resistance of aqueous humor outflow from the eye is the trabecular meshwork, in both the normal and glaucomatous eye. [Bill et al., Arch. Ophthal., 50:295 (1972); Rohen, Ophthal., 90:758 (1983)]. The trabecular meshwork of the rabbit and man are sufficiently similar to allow physiological and physio-chemical studies on the rabbit eye to apply to human glaucomatous conditions.

Current evidence indicates that one class of carbohydrate polymers, the glycosaminoglycans, act in regulating the rate of aqueous humor drainage through the trabecular meshwork. [Knepper et al., Exp. Eye Res., 32:3;265 (1981); Mathews, Mol. Biol., Biochem & Biophysics, 19:93 (1975); Comper et al., Physiol. Rev., 58:255 (1978); Zimmerman, Am. J. Ophthal., 44:1 (1957)]. The determination of the effect of anabolic androgen administration on glycosaminoglycan distribution was conducted as set forth below. These determinations show a metabolic effect upon the trabecular meshwork resulting from this drug therapy.

The metabolic effects of the application of selected steroids—dexamethasone, 17-alpha-methyltestosterone, or dexamethasone plus 17alpha-methyltestosterone —on glycosaminoglycan concentration, expressed as microgram per milligram of dry-defatted trabecular meshwork, were determined by high performance liquid chromatography using the following methods: One drop of the steroid, alone or in combination, was administered every six hours to each eye for four weeks. After the treatment period was completed and the intraocular pressure was measured (see Table 1), the eyes were enucleated, the trabecular meshwork was microdissected under a dissecting microscope and then frozen at $-20°$ C.

TABLE 1

Selected Steroids: Effect on Glycosaminoglycan Concentration in the Trabecular Meshwork of the Rabbit Eye

|  | Hyaluronic Acid (micrograms/mg/dry-defatted tissue) | Chondroitin Sulfate (micrograms/mg/dry-defatted tissue) |
| --- | --- | --- |
| Control | 0.589 | 1.601 |
| Dexamethasone | 0.150 | 2.860 |
| Testosterone | 0.389 | 2.254 |
| Dexamethasone | 0.660 | 1.083 |

TABLE 1-continued

Selected Steroids: Effect on
Glycosaminoglycan Concentration in the
Trabecular Meshwork of the Rabbit Eye

| | Hyaluronic Acid (micrograms/mg/dry-defatted tissue) | Chondroitin Sulfate (micrograms/mg/dry-defatted tissue) |
|---|---|---|
| plus Testosterone | | |

The glycosaminoglycans of the trabecular meshwork were isolated using methods which have been described (Knepper et al., Exp. Eye Res., 27:567-575, 1978). The trabecular meshwork was thawed at 4° C.; lipids were extracted with chloroform:methanol (2:1 volume/volume) for 1 hour (1 milliliter per 10 milligram dissected tissue); dried in vacuo at 50° C for 12 hours; and weighed. The lipid-free trabecular meshwork was digested at 50° C. for 24 hours with 0.4 percent Pronase B (Calbiochem-Behring, San Diego, CA) in 0.2 molar sodium borate buffer, pH 7.8, in two divided doses (at the start of the digestion and after 12 hours) to provide a total of 1 mg enzyme per 100 mg dry-defatted trabecular meshwork weight. The protein was removed by adding 80% trichloroacetic acid to obtain a final concentration of 5 percent trichloroacetic acid; the solution was centrifuged in a Sorvall Model RC-5 superspeed refrigerated centrifuge, (Dupont Instruments, Newtown, CT) at 12,000×g for 20 minutes. The supernatant was removed and the glycosaminoglycans were isolated by precipitation with 3 volumes of absolute ethanol containing 5% potassium acetate. After mixing, the solution was stored overnight at 4° C. and then centrifuged for 20 minutes at 12,000×g. The supernatant solution was discarded and the precipitated glycosaminoglycans were saved. The precipitate was washed with 2 milliliters of absolute ethanol, with 1:1 ethanol/ether and finally with 2 milliliters of ether alone. The glycosaminoglycans were dried in vacuo and dissolved in 0.075 molar sodium chloride.

The trabecular meshwork glycosaminoglycan samples were applied to a Sephadex G-50 column (1.6×22 cm) (Pharmacia Fine Chemicals, Piscataway, NJ) equilibrated with 0.1 M ammonium acetate, and separated by gel filtration chromatography. The trabecular meshwork glycosaminoglycans were collected from the excluded volume, and lyophilized to dryness. The concentration of the two major types of glycosaminoglycans of the trabecular meshwork was determined by enzymatic degradative procedures:

Hyaluronic acid was determined by its susceptibility to degradation by the specific enzyme, Streptomyces hyaluronate lyase (Enzyme Commission No. 4.2.99.1) (Miles Laboratories, Elkhart, IN): The incubation mixture (120 microliters) contained 1.0 unit enzyme and 2 micromoles of sodium acetate-15 micromoles sodium chloride, pH 5.0 and the isolated trabecular meshwork glycosaminoglycans. The reaction mixture was incubated at 60° C. for 2 hours. After completion of the procedure, 10 microliter aliquots were chromatographed by size exclusion high performance liquid chromatography using a Varian Model 5060 high performance liquid chromatograph (Varian Associates, Palo Alto, CA) equipped with a variable wavelength detector, an automatic injector valve (Rheodyne Incorporated, Cotati, CA), and a Varian Model 401 chromatography data system (Varian). Separation of the degradation products of hyaluronic acid from the enzyme resistant glycosaminoglycans was achieved by using two 0.75×300-mm Varian MicroPak TSK Gel PW 3000 columns (Varian), equipped with a Varian Guard column (Varian) packed with the same resin. Chromatographic elution was performed with 0.075 M sodium chloride at a flow rate of 1.0 milliliter per minute at 30° C. The eluate was monitored by measuring ultraviolet absorption at 232 nanometers. The degradation products of hyaluronic acid, delta-4,5-unsaturated glucopyranuronic acid-containing tetrasaccharides and hexasaccharides were measured in the included volume. The concentration of hyaluronic acid was calculated by integration of the area of included volume to a standard curve of known quantities of degradation products of hyaluronic acid.

Chondroitin sulfate was determined by its susceptibility to degradation by the specific enzyme, Proteus vulgaris chondroitin ABC lyase (Enzyme Commission No. 4.2.2.4) (Miles Laboratories): The incubation volume (120 microliters) contained 0.1 unit enzyme and 5 micromoles tris (hydroxymethyl)-aminomethane, 5.9 micromoles sodium acetate, 10 micrograms bovine serum albumin, pH 8.0, and the isolated trabecular meshwork glycosaminoglycans. The reaction mixture was incubated at 37° C. for 2 hours. After completion of the procedure, 10 microliter aliquots were chromatographed by size exclusion high performance liquid chromatography as previously described for the measurement of hyaluronic acid. The eluate was monitored by measuring ultraviolet absorption at 232 nanometers. The degradation products of chondroitin sulfate, delta-4,5- unsaturated glucopyranuronic acid-containing disaccharides, were measured in the included volume. The concentration of chondroitin sulfate was calculated by integration of the area under the curve representing the included volume to the area under a standard curve of known quantities of delta-4,5-unsaturated disaccharides minus the concentration of hyaluronic acid.

Thus, aqueous humor drainage through the trabecular meshwork may not be a question of simple fluid dynamics. A more salient hypothesis finds aqueous humor drainage to be a product of biochemical interactions within the trabeculum.

Therefore, a treatment is proposed that successfully reduces pathologic intraocular pressure with minimal side effects and which, by biochemical effect, may permanently alter the trabecular meshwork metabolism in a beneficial manner.

SUMMARY OF THE INVENTION

It has now been found that one or more members of the class of compounds characterized as anabolic androgens, when instilled into the eye, are effective in lowering elevated intraocular pressure. It has also been found that when these anabolic androgenic compounds are instilled into the eye concurrently with an intraocular pressure elevating substance such as a corticosteroid, the treatment regime prevents or blocks the untoward intraocular pressure elevating effect of corticosteroid administration. In a method aspect of this invention, these anabolic androgenic compounds are utilized to maintain normal or physiologic intraocular pressure. A further method aspect of this invention is useful for returning elevated intraocular pressure to normal or physiologic levels. The anabolic androgenic compounds contemplated by this invention are steroids having a nucleus generally constituted by a skeleton of 17 atoms together forming four fused rings.

In one aspect, this invention provides a composition useful for reducing pathological elevated intraocular pressure. The composition is comprised of an effective amount of an anabolic androgenic compound suitable for local administration to the eye and a pharmacologically acceptable carrier therefor. The composition contains an effective amount of the anabolic androgenic compound per administration. Such a composition is also useful for preventing elevated intraocular pressure secondary to intraocular pressure elevating pharmacologics or other intraocular pressure elevating factors found in the environment of a warm blooded animal. In the foregoing compositions, the anabolic androgenic compound is present preferably in a concentration of about 0.1 to about 10 percent by weight of the composition.

During treatment, the anabolic androgenic compound is administered to the eye by contacting the affected eye with a dosage in the range of about 0.001 milligrams to about 10 milligrams per administration, the preferred dosage range being about 0.004 to about 4.0 milligrams per administration. The administrations may be continuous or repeated over a period of time.

Preferred anabolic androgenic compounds for the purposes of this invention include 17-alpha-methyl-testosterone, oxandrolone, norethandrolone, bolasterone, methandrostenolone, oxymetholone and dihydrotestosterone.

DETAILED DESCRIPTION OF THE INVENTION

The following definitions apply to the terms set forth below as used herein: Anabolic Agent: A composition that promotes storage of protein and generally stimulates tissues.

Androgenic Agent: An agent that influences and promotes the male secondary sex characteristics.

Glaucoma: A group of disease states characterized by elevated intraocular pressure, cupping of the optic nerve and/or visual field loss.

Pathogenic Intraocular Pressure: Intraocular pressure of about 21 mm of mercury or greater as measured by Schiotz, MacKay-Marg or applanation tonometry.

Physiologic Intraocular Pressure: Intraocular pressure that is less than about 20 mm mercury when measured by standard tonometric techniques, also normal intraocular pressure.

Primary Glaucoma: These forms of glaucoma are not consistently associated with obvious systemic or other ocular disorders that might account for the alteration in outflow resistance.

Primary Open Angle Glaucoma: A disease state occurring in eyes presenting a deep anterior chamber and an open anterior chamber angle. The mechanism for alteration of the outflow resistance is unknown.

Secondary glaucoma: Characterized by associated ocular or systemic abnormalities that appear to be responsible for the alteration in resistence to aqueous outflow. In the detailed description of the invention, these conditions may be induced by intraocular pressure elevating pharmacologic therapies. (drug induced glaucoma).

Tonometry: Generally, the procedure utilized to measure the intraocular pressure by relating the deformation of the globe to the force responsible for the deformation. The two basic types of tonometers are indentation tonometers, where the shape of the deformation is a truncated cone (Schiotz tonometer), and applanation tonometers. Applanation tonometers create a deformation by a simple flattening. The shape of the deformation is constant allowing simple mathematical formulae to be utilized for calculation. The three types of applanation tonometers are (a) Variable force—this type measures the force required to flatten a standard area of the corneal surface (Goldman applanation, Mackay-Marg tonometer).

(b) Variable area—measures the area of the cornea flattened by a known force (Maklakov tonometry).

(c) Time—this type of tonometer measures the amount of time required to deform the cornea in response to a standard force, e.g., a puff of air (non-contact tonometer).

Unit Dosage Form: as used herein refers to physically discrete units suitable as unitary dosages for human patients and other warm blooded animals, each unit containing a predetermined quantity of the active ingredient calculated to produce the desired therapeutic effect in association with the required physiologically tolerable carrier, e.g. a diluent or a vehicle.

The specifications for the novel unit dosage forms of this invention are dictated by and are directly dependent on (a) the unique characteristics of the active ingredient and the particular therapeutic effect to be achieved, and (b) the limitations inherent in the art of compounding such an active ingredient for therapeutic use in humans and animals. Examples of suitable dosage forms in accord with this invention are ophthalmic drops, mucosal inserts, saturated contact lenses and the like, segregated multiples of any of the foregoing, as well as solutions and suspensions. A solution as utilized herein is a liquid homogeneous mixture where a solid or liquid form of the active ingredient is distributed throughout the carrier.

An anabolic androgenic steroid is contemplated as the active ingredient in the composition of the present invention. Such steroids are represented by the formula:

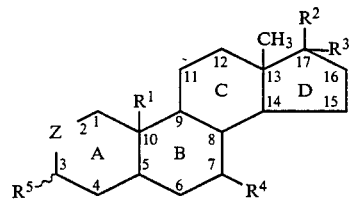

Wherein ring A is saturated or partially unsaturated, $R^1$ is a ring substituent in the C-10 position and a member of the group consisting of hydrogen and methyl;

$R^2$ is a beta substituent in the C-17 position and is a member of the group consisting of hydroxy and alkylcarbonyloxy containing up to six carbon atoms in the alkyl portion thereof;

$R^3$ is an alpha substituent in the C-17 position and a member of the group consisting of hydrogen and alkyl containing up to two carbon atoms in the alkyl portion thereof;

$R^4$ is a substituent in the C-7 position and a member of the group consisting of hydrogen and methyl.

Z is a divalent group forming a portion of ring A and a member of the group consisting of methylene, hydroxyvinylidene, methylmethylene and oxy; and $R^5$ is a monovalent or divalent substituent in the C-3 position and a member of the group consisting of oxo and hydroxy.

In ring A unsaturation can be present by the steroid having a double bond or bonds in the 1,2 and 4,5-positions or in the 4,5-position.

These compounds generally have primarily anabolic activity, primarily androgenic activity or both. The preferred compounds are generally steroids, although compounds with anabolic androgenic activity may be utilized in this invention Illustrative compounds possessing anabolic androgenic activity are set forth in the following Table 2.

TABLE 2
Anabolic Androgens 17-alpha-methyl-testosterone (17-hydroxy-17-methylandrost 4-en-3-one)

Dihydrotestosterone (5-alpha-androstan-17-beta-ol-3-one)

Androsterone (3-alpha-androstan-3-alpha-ol-17-one)

Dromostanolone propionate (17-beta-hydroxy-2-alpha-methyl-androstan-3-one-propionate)

Methandrostenelone (17-beta-hydroxy-16-methandrosta-1,4-dien-3-one)

TABLE 2-continued
Anabolic Androgens

Testosterone (17-beta-hydroxyandrost-4-en-3-one)

Testosterone enanthate (androst-4-en-3-one, 17-[(1-oxoheptyl)oxy)]-(17-beta))

Norethandrolone (17 alpha-ethyl-19-nortestosterone)

Bolasterone (17-hydroxy-7,17-dimethylandrost-4-en-3-one)

Oxymetholone (17-hydroxy-2-(hydroxymethylene)-17-methandrosterone-3-one)

oxandrolone (17-beta-hydroxy-17-methyl-2-oxa-androstan-3-one)

The above steroids possess anabolic androgenic activities and have a relative potency of at least about 0.3, and more preferably have a potency of at least about 0.5. Relative potency of androgenic effect determined by the chick comb induction test in oil yields a potency for testosterone of 1.0 (Fasman, *Handbook of Biochem.* and *Molec. Biol.*, 3d Ed, CRC Press/Boca Raton, Fl. (1975).

For example the relative potency of 19-nortestosterone is 0.72, dihydrotestosterone has a potency of 1.94, and 17-alpha-methyl testosterone has a potency of 1.45, androsterone has a potency of 1.64 and so on. The relative potency is taken into account in formulating an effective treatment regime.

Particularly preferred steroids are 17-alpha methyltestosterone and oxandrolone.

The amount of active ingredient that is to be administered depends on the age of the patient, the particular condition to be treated, the frequency of administration, and the route of administration. The concentration of active ingredient can range from about 0.01 percent to about 10 percent by weight in ophthalmic solution or about 0.001 milligram to about 10 milligram per administration. The most preferred concentration is about 0.004 milligram to about 4.0 milligrams per administration.

The human adult dose for an ophthalmic drop treatment regime is in the range of one drop in each eye about 1 to about 6 daily administrations. Veterinary dosages correspond to human dosages with the amounts administered being in proportion to the weight of the animal as compared to adult humans. The unit dose may be administered in a solution such as phosphate buffered saline (PBS).

The formulation may be more highly concentrated where, for example, additional ophthalmic therapeutics are to be admixed with the composition of this invention, thereby decreasing the amount of anabolic androgenic compound reaching actually administered to the eye.

The preferred concentration of anabolic androgenic compound is 0.1 percent to 5 percent by weight of active ingredient where the active ingredient has a potency of 0.27 or greater, (testosterone being assigned a potency of 1.0). Topical instillation of 1.0 percent by weight active ingredient in phosphate buffer measured at a one drop dosage at six (6) hour intervals has been found effective to lower elevated intraocular pressure or to prevent elevated intraocular pressure induced by corticosteroid administration. The dosage will depend upon the intraocular pressure response and the particular anabolic steroid employed.

In this invention a pharmacologically effective amount of an anabolic, androgenic or anabolic-androgenic substance was topically applied to the conjunctival sac wherein it was then absorbed through the interstitial spaces of the sclera or cornea by diffusion. The active ingredient thereby was directly absorbed into the trabecular meshwork of the affected eye. This administration regime results in a lowering of intraocular pressure.

The "effective amount" or "pharmacologically effective amount" of active ingredient in a unit dose depends upon a number of factors. Included among those factors are the carrier when used, the tolerance for the active ingredient, the response elicited, and the number of unit dose administrations desired to be used.

In this invention, anabolic androgenic compounds are administered to eyes exhibiting elevated intraocular pressure, usually presenting elevated intraocular pressure of 21 millimeters Hg or greater as measured with standard tonometric techniques such as Schiotz, MacKay Marg or applanation tonometry. Additional criteria for commencing the prescribed therapy are presentation of the standard diagnostic criteria for primary open angle glaucoma, such as glaucomatous field loss or optic nerve head damage.

In this invention the anabolic androgenic compounds are administered to eyes wherein there is a risk of induced elevated intraocular pressure, whether from corticosteroid therapy or from some other environmental or pharmacologic substance. Thus, the method of this invention may be applied to prevent induced elevated intraocular pressure as well as treating extant elevated intraocular pressure. The invention may also be applied to individuals to maintain normal or physiologic intraocular pressure.

The anabolic androgenic compounds constituting the active ingredients of the present invention are administered to the eyes topically in unit dose forms. The administered composition comprises a physiologically tolerable carrier and an effective amount of the active ingredient.

The topical instillation of the anabolic steroid avoids metabolic degradation of the biological activity of the drug by systemic digestion or removal of the active compound from systemic circulation by filtering or metabolic degradation in the liver. By-products or metabolites of systemically administered anabolic androgens are ineffective in the prevention of pharmacologically elevated intraocular pressure, or in the lowering of elevated intraocular pressure perhaps due to low concentration of these substances ultimately directed to the eye via systemic circulation.

The contemplated treatment regime of this invention requires application of a pharmacologically effective amount of active ingredient as described, in unit dose form, to an eye presenting elevated intraocular pressure, maintaining an effective unit dose amount applied for a sufficient period of time to assure that a lowered intraocular pressure is maintained. For example, intraocular pressure six months after a constant physiologic or normal intraocular pressure is obtained may be used as a benchmark to ensure that the affected eye is maintained at physiologic or normal eye pressure. The amount of active ingredient administered to the eye may be decreased after this point, either by decreasing the amount of active ingredient or decreasing the frequency of application of active ingredient in unit dose form to the eye. During this period of adjustment of dosage, the eye should be carefully monitored for any change in intraocular pressure or visual field.

The goal of this therapy regime is to maintain physiologic or normal intraocular pressure. Should it be found that a permanent alteration of the aqueous outflow mechanism is achieved through a biochemical alteration of the trabecular meshwork, such as presently postulated to be a biochemical alteration of metabolism of glycosaminoglycans, and should the patient present such a constant, permanently altered outflow facility, it may be possible to suspend all treatment with any anabolic or androgenic substance as is described in the preferred embodiment and the examples. A caveat should be followed in cessation of therapy, that being, regular monitoring of the intraocular pressure and visual field of eyes previously treated should continue throughout the life of the patient. Thus, early detection of any elevated intraocular pressure will be possible and the described treatment regime may again be employed to prevent subsequent glaucomatous visual field loss.

The contemplated treatment regime commences with 0.1 mg of active ingredient administered four times daily. As physiologic eye pressure is achieved and maintained, the total daily dose may be decreased to as little as 0.004 mg or less as is required to maintain the normal intraocular pressure. After one year of maintenance of intraocular pressure at a physiologic level, treatment may be ended and bi-monthly monitoring of intraocular pressure required for a period of six months to ensure that the normal intraocular pressure is maintained. If this desirable condition is continued, monitoring frequency may be decreased, with bi-annual checks of intraocular pressure and visual field continued to ensure that the glaucomatous condition or elevated intraocular pressure does not recur.

The treatment regime is effective in preventing secondary elevated intraocular pressure, a common side effect of corticosteriod therapy.

The treatment regime contemplated by this invention is effective in maintaining physiologic or normal intraocular pressure. The treatment regime is also effective in reducing elevated intraocular pressure, whether idiopathic or induced.

Application of anabolic androgenic suspensions to dexamethasone-treated eyes reduces elevated intraocular pressure induced by corticosteroid treatment. When a selected anabolic androgen is applied to the eye concurrently with dexamethasone, elevated intraocular pressure does not occur. In the latter instance, the proposed treatment regime will consist of concurrent administration of an effective unit dose of the anabolic androgenic compound concurrently with the intraocular pressure elevating compound. This treatment may be halted when the pressure elevating compound is metabolically removed completely from the affected individual's systemic or ocular circulation.

Suitable pharmacologic carriers for the foregoing anabolic androgenic steroids are an aqueous solution, oil suspension, lanolin petrolatum ointment or solid insert such as is commercially available under the designation such as Ocusert® (Ciba Pharmaceutical Co., Summit, N.J.) Ophthalmic solutions may contain the pharmacologically effective anabolic androgenic steroid in amounts ranging from 0.01 percent to 10 percent by weight. In the most preferred embodiment, the anabolic androgenic steroid is present preferably from about 0.1 percent to 5 percent by weight.

The method of administration of the anabolic androgenic steroid involves suspending the compound in an appropriate carrier or utilizing subconjunctival injection of a selected active ingredient, or introducing it in such a way that the active ingredient, such as 17-alpha-methyl-testosterone, contacts the cornea of the eye where it is absorbed directly into the eye. A subconjunctival injection is formulated utilizing an oil suspension to ensure slow release of the anabolic androgenic compound. In this instance, a saturated solution of anabolic androgenic compound will form the major constituent of the composition.

The anabolic androgenic compounds pass through the cornea and sclera by diffusion, acting on the trabecular meshwork whereupon beneficial modification of the rate of aqueous humor outflow is effected. For example, a saturated contact lens could allow controlled release of the composition. Thus, a contact lens saturated with 17-alpha-methyl-testosterone as the anabolic androgen would allow continuous administration of the active ingredient. Any systemic administration of the active ingredient would have no ophthalmic effect due to systemic metabolic degradation. A controlled release device would thereby avoid the metabolic degradation resulting from administration parenteral or intramuscular administration.

Several methods of ophthalmic administration in addition to the most preferred saturated contact lens are possible. Any route of ophthalmic administration that ensures that the active ingredient diffuses through the cornea thereby reaching the trabecular meshwork is effective. These routes of administration include suspending the compound in a liquid carrier with the appropriate pH such as an isotonic aqueous sodium chloride vehicle, conventional phosphate buffer vehicle systems, isotonic sodium borate vehicle systems, or the like and applying the active compound directly to the cornea and sclera of the eye by instilling drops into the conjunctival sac. These methods include use of ophthalmic ointments, solutions, subconjunctival injection of a suspension of the active ingredient, or solid inserts to release the active ingredient.

The pharmaceutical preparation may also contain additional components such as emulsifying, preserving, wetting and sterilizing agents. The carrier that the selected anabolic androgenic substance is suspended in possesses no known intrinsic pharmacological activity.

A particularly preferred route of administration is a contact lens system wherein the active ingredient is thereby topically administered to the cornea continuously while vision is unimpaired and administration of the active ingredient uninterrupted as occurs in treatment regimes specifying the instillation of drops. A saturated contact lens would have a highly concentrated amount of the anabolic androgen to assure a sufficient amount of the active ingredient reaches the trabecular meshwork over the period of continuous administration.

A variety of treatment regimes are therefore possible, and the invention as described relates to the administration of one or a variety of anabolic androgenic compounds to achieve the result of maintaining physiologic intraocular pressure or lowering elevated intraocular pressure by the administration of an active ingredient such as 17-alpha-methyl-testosterone, oxandrolone or analogous anabolic androgenic substances. The administration of the active ingredient is by means of ophthalmic administration.

Consequently, such compounds are useful for the treatment of primary open angle glaucoma and corticosteroid induced ocular hypertension or prevention of induced (secondary) elevated intraocular pressure since the compounds directly diffuse through the cornea and sclera whereupon the selected compound may alter the metabolism of the trabecular meshwork of the eye thereby facilitating physiologic aqueous humor outflow resulting in normal intraocular pressure. Any intraocular pressure reducing effect would be lost if the compound were systemically administered due to metabolic degradation in the liver.

The preferred embodiment to be utilized in this invention requires a determination that the eye presents clinical findings, as determined by standard methods, indicating glaucoma. These findings include unphysiological eye pressure, optic nerve damage or visual field loss, whether induced by corticosteroid administration or resulting from spontaneous primary open angle glaucoma. The affected eye is then treated with a solution of a selected anabolic androgenic compound at prescribed intervals over a predetermined period of time. The active ingredient is suspended in an appropriate carrier and instilled into the affected eye utilizing an ophthalmic drop, and administered at these intervals in the prescribed dosages yields consistent reduction in intraocular pressure. The following examples more fully illustrate the invention. These examples are not intended to be limiting.

EXAMPLE 1

New Zealand rabbits received 0.1 percent dexamethasone solution instilled into both eyes at 6 hour intervals for a period of two weeks. Dexamethasone administration resulted in an increase of intraocular pressure in both eyes of the rabbit (corticosteroid induced glaucoma). Following the two weeks of dexamethasone administration in both eyes, the right eye of the rabbits received a treatment regime consisting of a 1.0 percent 17-alpha-methyl-testosterone, in a phosphate buffered saline solution and a 0.1 percent dexamethasone solution administered concurrently whereas the left eye received a 0.1 percent dexamethasone solution alone. Following the concurrent administration of the 17-alpha-methyl-testosterone and dexamethasone solutions, the elevated intraocular pressure in the treated eye was reduced to normal levels.

The dexamethasone and 17-alpha-methyl testosterone solutions were administered alone or of one or both solutions (about 0.04 ml) to each eye about every 6 hours for 4 weeks. A sterile, isotonic phosphate buffer suspension of 17-alpha-methyl-testosterone is prepared by dissolving 1.0 gram in 100 ml of the phosphate buffer to give a 1% solution. A commercial preparation of 0.1% dexamethasone commonly available under the trade name Decadron ® (Merck Sharp & Dohme, West Point, PA) was used to increase ocular hypertension as described by Knepper, P.A., et al., Exp. Eye Res., 27:567 (1978). The test results are shown in Table 3.

TABLE 3

| INTRAOCULAR PRESSURE+ MEASUREMENT: Dexamethasone/17-alpha-methyl-testosterone | | |
|---|---|---|
| Week of Treatment | Right Eye$^o$ | Left Eye$^o$ |
| 0 | 20.0 ± 1.9 | 20.7 ± 1.8 |
| 1 | 21.4 ± 1.3 | 21.1 ± 1.3 |
| 2 | 30.0 ± 5.2 | 28.9 ± 4.5 |
| 3 | 23.6 ± 1.5 | 31.0 ± 4.2 |
| 4 | 21.1 ± 1.8$^{ab}$ | 31.0 ± 4.1 |

Table entries are the mean intraocular pressure, mm Hg, ± the standard deviation for seven rabbit eyes.
+Intraocular pressure was measured by MacKay-Marg tonometry.
$^o$The right eye received 0.1 percent dexamethasone ophthalmic drop alone every 6 hours for 2 weeks and then was treated with the 1.0% 17-alpha-methyl-testosterone-0.1% dexamethasone ophthalmic drop of each every 6 hours for 2 weeks. The left eye received 0.1 percent dexamethasone ophthalmic drop alone every 6 hours for 4 weeks.
$^a$p less than 0.001 when compared to 2 week right eye value.
$^b$p less than 0.001 when compared to 4 week left eye value.

The validity of the tonometer measurements performed on the experimental animals to determine intraocular pressure was evaluated by a closed and an open manometric system. The tonometer was highly reliable; the goodness of fit ($r^2$) being 0.963 (closed) and 0.940 (open) with intraocular pressure up to 60 mm Hg for control eyes, 0.887 and 0.958 for eyes treated 2 weeks with dexamethasone, and 0.893 and 0.755 for eyes treated 4 weeks with deaxmethasone. In addition, the results of tonometry recordings with a pneumatonograph method were similar to results with the MacKay-Marg method. The results of these studies indicate that the topical administration of dexamethasone induces ocular hypertension in the experimental animals utilized, young New Zealand rabbits.

EXAMPLE 2

Normal New Zealand Red Rabbits (10 weeks of age; 1.4 to 1.9 Kg) were treated with 17-alpha-methyl-testosterone and dexamethasone in combination, dexamethasone alone, or a control solution (isotonic saline solution). The dexamethasone and 17-alpha-methyl testosterone solutions, alone or in combination, were administered by the topical instillation of one drop of one or both compounds (about 0.04 ml) to each eye about every 6 hours for 4 weeks. The sterile, isotonic phosphate buffer suspension of 17-alpha-methyl-testosterone administered to the rabbits was prepared by dissolving 1.0 gram in 100 ml of the phosphate buffer to give a 1% solution. A commercial preparation of 0.1% dexamethasone (Decadron ®), was used to increase ocular hypertension as described by Knepper, P.A., et al., Exp. Eye Res., 27:567 (1978).

The result of 17-alpha-methyl-testosterone administration in conjunction with dexamethasone administration was that the intraocular pressure was unaffected in eyes receiving the anabolic androgen and the corticosteroid. This is in contrast to the marked elevation in intraocular pressure found in the dexamethasone administration without the 17-alpha-methyl-testosterone. From these results it can be seen that 17-alpha-methyl-testosterone effectively blocked the adverse reaction to dexamethasone. Additionally, there was a slight decrease in intraocular pressure of 62 eyes treated with 17-alpha-methyl-testosterone alone and a marked increase in intraocular pressure of 5 mm Hg or more in 114 of 138 eyes treated with dexamethasone alone. Intraocular pressure remained unchanged in the eyes treated with dexamethasone and 17-alpha-methyl-testosterone concurrently, effectively blocking the intraocular pressure elevating effect of dexamethasone alone. Thus, the concurrent administration of dexamethasone plus 17-alpha-methyl-testosterone had no effect on intraocular pressure indicating that the anabolic androgenic compound blocked or prevented corticosteroid induced elevated intraocular pressure. See Table 4, below.

TABLE 4

| INTRAOCULAR PRESSURE+ MEASUREMENT AND -17-alpha-methyl-testosterone | | | | | | |
|---|---|---|---|---|---|---|
| | | Weeks of Treatment | | | | |
| Treatment | n | 0 | 1 | 2 | 3 | 4 |
| Control | 82 | 19.3 ± 1.3 | 19.3 ± 1.0 | 19.2 ± 1.1 | 19.0 ± 1.0 | 18.0 ± 0.9 |
| Dexamethasone, alone$^o$ | 138 | 18.7 ± 1.5 | 19.0 ± 2.0 | 23.9 ± 2.8$^{a,b}$ | 25.5 ± 2.6$^{a,b}$ | 26.8 ± 3.2$^a$,* |
| 17-alpha-methyl-testosterone, alone | 62 | 19.3 ± 1.1 | 19.1 ± 1.1 | 19.1 ± 0.9 | 18.9 ± 1.0 | 18.7 ± 1.0 |
| 17-alpha-methyl-testosterone-Dexamethasone, | 42 | 19.6 ± 1.8 | 20.5 ± 1.3 | 20.8 ± 1.7 | 21.2 ± 2.2 | 20.8 ± 3.7 |

TABLE 4-continued

INTRAOCULAR PRESSURE+ MEASUREMENT AND -17-alpha-methyl-testosterone

| Treatment | n | Weeks of Treatment | | | | |
|---|---|---|---|---|---|---|
| | | 0 | 1 | 2 | 3 | 4 |
| in combination | | | | | | |

Table entries are the mean intraocular pressure mm Hg ± standard deviation.
+Intraocular pressure was measured by MacKay-Marg tonometry.
$^o$Steroid or control (phosphate buffer, M/15, pH 7.4) were administered by the topical instillation of ophthalmic drop every 6 hours for 4 weeks.
n Number of eyes tested.
$^a$p less than 0.001 when compared to the control values.
$^b$p less than 0.001 when compared to the dexamethasone-17-alpha-methyl-testosterone values.

EXAMPLE 3

The experiment of Example 2 was repeated in all essential detail except that a different member of the class of anabolic androgenic compounds, oxandrolone, commonly available under the trademark Anavar ® (G. D. Searle & Co., Sam Juan, Puerto Rico), was used to determine its intraocular pressure lowering effect. The physiologic effect of oxandrolone administration was found to be about the same as that of 17-alpha-methyl-testosterone.

The intraocular pressure lowering effect of oxandrolone was conducted to determine the intraocular pressure lowering effects of this member class of anabolic androgenic steroids. The dexamethasone and oxandrolone solutions were administered by the topical instillation of one drop (about 0.04 ml) to each eye about every 6 hours for 4 weeks. The sterile, isotonic phosphate buffer suspension of oxandrolone used in this Example was prepared by dissolving 0.1 gram of oxandrolone in 100 ml of the phosphate buffer to give a 0.10 percent solution. A commercial preparation of 0.1 percent dexamethasone (Decadron ®), was used to increase ocular hypertension as described by Knepper, P.A., et al., Exp. Eye Res., 27:567 (1978). The test results are shown in Table 5.

The concurrent administration of oxandrolone and dexamethasone resulted in no elevation of intraocular pressure. Thus, this member of the class of anabolic androgenic compounds effectively blocked any corticosteroid induced elevation of intraocular pressure.

The administration of 17-alpha-methyl-testosterone or oxandrolone blocked the effect of the dexamethasone as was seen in Examples 2 and 3. In Example 1, the 17-alpha-methyl-testosterone achieved a reversal of the elevation of the intraocular pressure induced in the rabbit eye through the administration of dexamethasone. No statistically significant reduction in intraocular pressure was achieved by the administration of 17-alpha-methyl-testosterone or oxandralone alone. Thus, the administration of either 17-alpha-methyl-testosterone or oxandrolone successfully prevented elevation of the intraocular pressure induced by dexamethasone administration. The administration of 17-alpha-methyl-testosterone successfully reversed the elevation of intraocular pressure induced by dexamethasone administration. The elevation of intraocular pressure by administration of dexamethasone was of a degree of severity such as may occur in primary open angle glaucoma. Glaucoma was induced in these animals due to the unavailability of suitable experimental animals with spontaneously occurring primary open angle glaucoma. It is believed that the pressure lowering effect of 17-alpha-methyl-testosterone and oxandrolone will be equivalent in spontaneously occurring or induced or secondary open angle glaucoma in humans.

EXAMPLE 4

The experiment of Example 1 is repeated in all essential detail except that a different member of the class of anabolic androgenic steroids, dihydrotestosterone, is used to determine its intraocular pressure lowering effect.

The intraocular pressure lowering effect of dihydrotestosterone conducted to determine the intraocular pressure lowering effects of this member of the class of anabolic androgenic steroids. The dexamethasone and dihydrotestosterone solutions, administered alone or concurrently, are to be topically instilled at the dosage of one drop (about 0.04 ml) to each eye about every 6 hours for 4 weeks. A sterile, isotonic phosphate buffer suspension of dihydrotestosterone is prepared by dissolving 1.0 gram in 100 ml of the phosphate buffer to give a 1% solution. A commercial preparation of 0.1% dexamethasone (Decadron ®) is used as before to increase ocular hypertension as described by Knepper, P.A., et al., Exp. Eye Res., 27:567 (1978).

TABLE 5

INTRAOCULAR PRESSURE+ MEASUREMENT
Dexamethasone and 17-beta-hydroxy-17-alpha-methyl-2-oxa-5-alpha-androstan-3-one: (Oxandrolone)

| Treatment | n | Weeks of Treatment | | | | |
|---|---|---|---|---|---|---|
| | | 0 | 1 | 2 | 3 | 4 |
| Dexamethasone$^o$, alone | 138 | 18.7 ± 1.5 | 19.0 ± 2.0 | 23.9 ± 2.8 | 25.5 ± 2.6 | 26.8 ± 3.2$^a$ |
| Oxandrolone$^o$ alone | 10 | 19.4 ± 1.7 | 20.7 ± 1.5 | 19.4 ± 1.5 | 20.5 ± 2.0 | 19.7 ± 1.2 |
| Oxandrolone$^o$-Dexamethasone, in combination | 10 | 19.7 ± 0.5 | 20.4 ± 1.0 | 21.6 ± 1.1 | 21.1 ± 2.0 | 19.3 ± 1.3 |

Table entries are the mean intraocular pressure mm Hg ± standard deviation.
+intraocular pressure pressure was measured by MacKay-Marg tonometry.
$^o$Dexamethasone and/or oxandrolone were administered by topical instillation of one ophthalmic drop in each eye every 6 hours for 4 weeks.
$^a$p less than 0.001 when compared to the dexamethasone-oxandrolone values.

In a manner similar to Example 1, the intraocular pressure elevating effects of dexamethasone administration are reversed by the administration of dihydrotestosterone.

EXAMPLE 5

The experiment of Example 2 is repeated in all essential detail except that a different member of the class of anabolic androgenic compounds, dihydrotestosterone is used to determine its intraocular pressure lowering effect.

The intraocular pressure lowering effect of dihydrotestosterone is conducted to determine the intraocular pressure lowering effects of this member of the class of anabolic androgenic steroids. The steroid solutions, alone or concurrently, are administered by the topical instillation of one drop (about 0.04 ml) to each eye about every 6 hours for 4 weeks. The sterile, isotonic phosphate buffer suspension of Dihydrotestosterone is prepared by dissolving 1.0 gram in 100 ml of the phosphate buffer to give a 1% solution. A commercial preparation of 0.1% dexamethasone (Decadron ®), is used to increase ocular hypertension as described by Knepper, P.A., et al., Exp. Eye Res., 27:567 (1978).

In a manner similar to Example 2, the intraocular pressure elevating effects of dexamethansone administration are blocked by the administration of dihydrotestosterone concurrently with the dexamethasone.

EXAMPLE 6

The experiment of Example 1 is repeated in all essential detail except that a different member of the class of anabolic androgenic steroids, androsterone, is used to determine its intraocular pressure lowering effect.

The intraocular pressure lowering effect of androsterone is utilized to determine the effect the intraocular pressure lowering effects of this member of the class of anabolic angrogenic steroids. The dexamethasone and androsterone solutions, alone or in combination, are to be administered by the topical instillation of one drop (about 0.04 ml) to each eye about every 6 hours for 4 weeks. A sterile, isotonic phosphate buffer suspension of androsterone is prepared by dissolving 1.0 gram in 100 ml of the phosphate buffer to give a 1% solution. A commercial preparation of 0.1% dexamethasone (Decadron ®), is used to increase ocular hypertension as described by Knepper, P.A., et al., Exp. Eye Res., 27:567 (1978).

In a manner similar to Example 1, the intraocular pressure elevating effects of dexamethasone administration are reversed by the administration of androsterone.

EXAMPLE 7

The experiment of Example 2 is repeated in all essential detail except that a different member of the class of anabolic androgenic compounds, androsterone, is used to determine its intraocular pressure lowering effect.

The intraocular pressure lowering effect of androsterone is evaluated to determine the effects of this member of the class of anabolic androgenic steroids in preventing elevated intraocular pressure. The steroid solutions, alone or by concurrent administration of both solutions, are administered by the topical instillation of one drop (about 0.04 ml) to each eye about every 6 hours for 4 weeks. A sterile, isotonic phosphate buffer suspension of androsterone is prepared by dissolving 1.0 gram in 100 ml of the phosphate buffer to give a 1% solution. A commercial preparation of 0.1% dexamethasone (Decadron ®), is used as described in the examples above.

In a manner similar to Example 2 the intraocular pressure elevating effects of dexamethasone are blocked or prevented by the concurrent administration of androsterone and the corticosteroid, e.g., dexamethasone.

EXAMPLE 8

The experiment of Example 1 is repeated in all essential detail except that a different member of the class of anabolic androgenic steroids, norethandrolone, is used to determine its intraocular pressure lowering effect.

Norethandrolone is utilized to effectuate the intraocular pressure lowering effects of this member of the class of anabolic androgenic steroids. The dexamethasone and norethandrolone solutions, alone or in combination, are to be administered by the topical instillation of one drop (about 0.04 ml) to each eye about every 6 hours for 4 weeks. A sterile, isotonic phosphate buffer suspension of norethandrolone is prepared by dissolving 1.0 gram in 100 ml of the phosphate buffer to give a 1% solution. A commercial preparation of 0.1% dexamethasone (Decadron ®), is used as described in the examples above.

In a manner similar to Example 1, the intraocular pressure elevating effects of dexamethasone administration are reversed by the administration of Norethandrolone.

EXAMPLE 9

The experiment of Example 2 is repeated in all essential detail except that a different member of the class of anabolic androgenic compounds, norethandrolone, is used to determine its intraocular pressure lowering effect.

Norethandrolone is utilized to prevent the intraocular pressure effects of corticosteroids. The steroid solutions, alone or by concurrent administration of both solutions, are administered by the topical instillation of one drop (about 0.04 ml) to each eye about every 6 hours for 4 weeks. A sterile, isotonic phosphate buffer suspension of Norethandrolone is prepared by dissolving 1.0 gram in 100 ml of the phosphate buffer to give a 1% solution. A commercial preparation of 0.1% dexamethasone (Decadron ®), is used as described in the example above.

In a manner similar to Example 2 the intraocular pressure elevating effects of dexamethasone are blocked or prevented by the concurrent administration of norethandrolone and the corticosteroid, e.g., dexamethasone.

EXAMPLE 10

The experiment of Example 1 is repeated in all essential detail except that a different member of the class of anabolic androgenic steroids, bolasterone, is used to determine its intraocular pressure lowering effect.

Bolasterone is utilized to effectuate the intraocular pressure lowering effects of this member of the class of anabolic androgenic steroids. The dexamethasone and bolasterone solutions, alone or in combination, are to be administered by the topical instillation of one drop (about 0.04 ml) to each eye about every 6 hours for 4 weeks. A sterile, isotonic phosphate buffer suspension of bolasterone is prepared by dissolving 1.0 gram in 100 ml of the phosphate buffer to give a 1% solution. A commercial preparation of 0.1% dexamethasone (Decadron ®), is used as described in the above example.

In a manner similar to Example 1, the intraocular pressure elevating effects of dexamethasone administration are reversed by the administration of bolasterone.

EXAMPLE 11

The experiment of Example 2 is repeated in all essential detail except that a different member of the class of anabolic androgenic compounds, bolasterone, is used to determine its intraocular pressure lowering effect.

Bolasterone is utilized to prevent the intraocular pressure effects of corticosteroids. The steroid solutions, alone or in concurrent administration of both solutions, are administered by the topical instillation of one drop (about 0.04 ml) to each eye about every 6 hours for 4 weeks. A sterile, isotonic phosphate buffer suspension of bolasterone is prepared by dissolving 1.0 gram in 100 ml of the phosphate buffer to give a 1% solution. A commercial preparation of 0.1% dexamethasone (Decadron ®), is used as described in the example above.

In a manner similar to Example 2 the intraocular pressure elevating effects of dexamethasone are blocked or prevented by the concurrent administration of bolasterone and the corticosteroid, e.g., dexamethasone.

EXAMPLE 12

The experiment of Example 1 is repeated in all essential detail except that a different member of the class of anabolic androgenic steroids, methandrostenolone, is used to determine its intraocular pressure lowering effect.

Methandrostenolone is utilized to effectuate the intraocular pressure lowering effects of this member of the class of anabolic androgenic steroids. The dexamethasone and methandrostenolone solutions, alone or in combination, are to be administered by the topical instillation of one drop (about 0.04 ml) to each eye about every 6 hours for 4 weeks. A sterile, isotonic phosphate buffer suspension of methandrostenolone is prepared by dissolving 1.0 gram in 100 ml of the phosphate buffer to give a 1% solution. A commercial preparation of 0.1% dexamethasone (Decadron ®), is used as described in the above example.

In a manner similar to Example 1, the intraocular pressure elevating effects of dexamethasone administration are reversed by the administration of methandrostenolone.

EXAMPLE 13

The experiment of Example 2 is repeated in all essential detail except that a different member of the class of anabolic androgenic compounds, methandrostenolone, was used to determine its intraocular pressure lowering effect.

Methandrostanolone is utilized to prevent the intraocular pressure effects of corticosteroids. The steroid solutions, alone or in concurrent administration of both solutions, are administered by the topical instillation of one drop (about 0.04 ml) to each eye about every 6 hours for 4 weeks. A sterile, isotonic phosphate buffer suspension of methandrostanolone is prepared by dissolving 1.0 gram in 100 ml of the phosphate buffer to give a 1% solution. A commercial preparation of 0.1% dexamethasqne (Decadron ®), is used as described in the example above.

In a manner similar to Example 2 the intraocular pressure elevating effects of dexamethasone are blocked or prevented by the concurrent administration of methandrostenolone and the corticosteroid, e.g., dexamethasone.

EXAMPLE 14

The experiment of Example 1 is repeated in all essential detail except that a different member of the class of anabolic androgenic steroids, oxymetholone, used to determine its intraocular pressure lowering effect.

Oxymetholone is utilized to effectuate the intraocular pressure lowering effects of this member of the class of anabolic androgenic steroids. The dexamethasone and oxymetholone solutions, alone or in combination, are to be administered by the topical instillation of one drop (about 0.04 ml) to each eye about every 6 hours for 4 weeks. A sterile, isotonic phosphate buffer suspension of oxymetholone is prepared by dissolving 1.0 gram in 100 ml of the phosphate buffer to give a 1% solution. A commercial preparation of 0.1% dexamethasone (Decadron ®), is used as described in the above example.

In a manner similar to Example 1, the intraocular pressure elevating effects of dexamethasone administration are reversed by the administration of oxymetholene.

EXAMPLE 15

The experiment of Example 2 is repeated in all essential detail except that a different member of the class of anabolic androgenic compounds, oxymetholone, was used to determine its intraocular pressure lowering effect.

Oxymetholone is utilized to prevent the intraocular pressure effects of corticosteroids. The steroid solutions, alone or in concurrent administration of both solutions, are administered by the topical instillation of one drop (about 0.04 ml) to each eye about every 6 hours for 4 weeks. A sterile, isotonic phosphate buffer suspension of oxymetholone is prepared by dissolving 1.0 gram in 100 ml of the phosphate buffer to give a 1% solution. A commercial preparation of 0.1% dexamethasone (Decadron ®), is used as described in the example above.

In a manner similar to Example 2 the intraocular pressure elevating effects of dexamethasone are blocked or prevented by the concurrent administration of oxymetholone and the corticosteroid, e.g., dexamethasone.

Any one of several other anabolic androgenic compounds may be substituted for the particular active ingredient in Examples 1 through 15. Likewise, the amount of active ingredient in these illustrative examples may be varied to achieve an effective dose range to obtain an intraocular pressure lowering effect in an affected eye.

The foregoing specification and the Examples are intended as illustrative of the present invention and are not to be taken as limiting. Still other compositions and methods of treatment are possible without departing from the spirit and scope of this invention as will be readily apparent to those skilled in the art.

What is claimed is:

1. A method for reducing elevated intraocular pressure in an eye of a warm blooded animal that comprises contacting the eye repeatedly with a composition containing as an active ingredient an anabolic androgenic compound which is a member of the group consisting of 17-alpha-ethyl-19-nortestosterone, 17-hydroxy-7,17-dimethylandrost-4-en-3-one, 17-beta-hydroxy-16-methandrost-1,4-dien-3-one, 17-hydroxy-2-(hydroxymethylene)-17-methylandrosterone-3-one, dihydrotestosterone, and androsterone, and providing to the eye about 0.001 milligrams to about 10 milligrams of said compound per application.

2. A method for reducing elevated intraocular pressure in an eye of a warm blooded animal that comprises contacting the eye repeatedly with a composition containing as an active ingredient oxandrolone together with a pharmacologically acceptable carrier therefor and providing to the eye about 0.001 milligrams to about 10 milligrams of oxandrolone per application.

3. The method of claim 1 wherein the anabolic androgenic compound is 17-alpha-ethyl-19-nortestosterone.

4. The method of claim 1 wherein the anabolic androgenic compound is 17-hydroxy-7,17-dimethylandrost-4-en-3-one.

5. The method of claim 1 wherein the anabolic androgenic compound is 17-beta-hydroxy-16-methandrost-1,4-dien-3-one.

6. The method of claim 1 wherein the anabolic androgenic compound is 17-hydroxy-2-(hydroxymethylene)-17-methylandrosterone-3-one.

7. The method of claim 1 wherein the anabolic androgenic compound is dihydrotestosterone.

8. The method of claim 1 wherein the anabolic androgenic compound is androsterone.

9. The method of preventing elevated intraocular pressure in a warm blooded animal secondary to administration of an intraocular pressure elevating composition which comprises repeatedly contacting an affected eye with an effective amount of composition containing active ingredient an anabolic androgenic compound which is a member of the group consisting of oxandrolone, 17-alpha-ethyl-19-nortestosterone, 17-hydroxy-7,17-dimethylandrost-4-en-3-one, 17-beta-hydroxy-16-methandrost-1,4-dien-3-one, 17-hydroxy-2-(hydroxymethylene)-17-methylandrosterone-3-one, dihydrotestosterone, and androsteone.

10. The method of claim 9 wherein said composition contains said anabolic androgenic compound in a concentration sufficient to supply from about 0.001 milligrams to about 10 milligrams of the anabolic androgenic compound per application.

11. The method of claim 9 wherein said composition contains an amount of said anabolic androgenic compound in a concentration sufficient to supply from about 0.004 milligrams to about 4.0 milligrams of the anabolic androgenic per application.

12. The method of claim 9 wherein the anabolic androgenic compound is oxandrolone.

13. The method of claim 9 wherein the anabolic androgenic compound is 17-alpha-ethyl-19-nortestosterone.

14. The method of claim 9 wherein the anabolic androgenic compound is 17-hydroxy-17-dimethylandrost-4-en-3-one.

15. The method of claim 9 wherein the anabolic androgenic compound is 17-beta-hydroxy-16-methandrost-1,4-dien-3-one.

16. The method of claim 9 wherein the anabolic androgenic compound is 17-hydroxy-2-(hydroxymethylene)-17-methylandrosterone-3-one.

17. The method of claim 9 wherein the anabolic androgenic compound is dihydrotestosterone.

18. The method of claim 9 wherein the anabolic androgenic compound is androsterone.

19. A method for maintaining a substantially normal intraocular pressure in a warm blooded animal receiving an administration of an intraocular pressure elevating compound that comprises contacting the eye substantially concurrently with said administration of said intraocular pressure elevating compound and repeatedly with an effective amount of a composition containing as an active ingredient an anabolic androgenic compound which is a member of the group consisting of oxandrolone, 17-hydroxy-2-(hydroxymethylene)-17-methylandrosterone-3-one, dihydrotestosterone, androsterone, 17-alpha-ethyl-19-nortestosterone, 17-hydroxy-7,17-dimethylandrost-4-en-3-one, and methandrostenolone.

20. The method of claim 19 wherein said anabolic androgenic compound is oxandrolone.

21. The method of claim 19 wherein said anabolic androgenic compound is 17-hydroxy-2-(hydroxymethylene)-17-methylandrosterone-3-one.

22. The method of claim 19 wherein said anabolic androgenic compound is dihydrotestosterone.

23. The method of claim 19 wherein said anabolic androgenic compound is androsterone.

24. The method of claim 19 wherein said anabolic androgenic compound is 17-alpha-ethyl-19-nortestosterone.

25. The method of claim 19 wherein said anabolic androgenic compound is 17-hydroxy-7,17-dimethylandrost-4-en-3-one.

26. The method of claim 19 wherein said anabolic androgenic compound is methandrostenolone.

27. A method of preventing elevated intraocular pressure induced by an intraocular pressure elevating compound in a warm blooded animal which method comprises the steps of
preparing a composition containing oxandrolone; and
repeatedly administering an effective amount of the composition to an eye of the animal over a period of time at predetermined intervals substantially concurrently with the administration of an intraocular pressure elevating compound.

28. A method of reducing elevated intraocular pressure in a warm blooded animal comprising the steps of
preparing a composition comprised of oxandrolone and a physiologically tolerable carrier therefor; and
repeatedly administering an effective amount of the composition to an eye of the animal over a period of time at predetermined intervals.

* * * * *